(12) United States Patent
Mullejans et al.

(10) Patent No.: US 8,704,033 B2
(45) Date of Patent: *Apr. 22, 2014

(54) DEVICE FOR RECORDING AND TRANSFERRING A CONTOUR

(75) Inventors: Peter Mullejans, Aalsgaarde (DK); Betina Toelboell Nielsen, Kvistgaard (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,792

(22) Filed: May 2, 2011

(65) Prior Publication Data

US 2011/0203466 A1   Aug. 25, 2011

Related U.S. Application Data

(63) Continuation of application No. 11/920,738, filed as application No. PCT/DK2006/000277 on May 19, 2006.

(51) Int. Cl.
*A61F 13/00* (2006.01)
(52) U.S. Cl.
USPC ................................. 602/41; 602/42; 602/52

(58) Field of Classification Search
USPC ........ 602/42–56; 128/888, 889; 604/304, 307
See application file for complete search history.

(56) References Cited

U.S. PATENT DOCUMENTS

| | | | |
|---|---|---|---|
| 4,787,380 A * | 11/1988 | Scott ............................... | 602/52 |
| 5,605,165 A * | 2/1997 | Sessions et al. ............... | 128/888 |
| 5,968,000 A * | 10/1999 | Harrison et al. ................ | 602/41 |
| 6,222,090 B1 * | 4/2001 | Weston ........................... | 602/41 |
| 6,359,100 B1 * | 3/2002 | Hostettler et al. .............. | 528/58 |

* cited by examiner

*Primary Examiner* — Michael A. Brown
(74) *Attorney, Agent, or Firm* — Coloplast Corp., Coloplast A/S; Nick Baumann

(57) ABSTRACT

A device for recording and transferring the contours of a wound or opening in tissue of a human being to an adhesive wafer of a wound appliance is provided. The device includes a transparent polymer sheet having a first and a second surface, the first surface being non-adhesive and facing the wound or opening and the second surface having a central portion and an edge portion, with the edge portion being provided with an adhesive layer. The device is placed over the wound or opening and the contours are traced on the central portion of the device. The adhesive layer on the second surface is then adhered to the wafer so that the drawn image contacts the wafer and is directly imparted to the wafer.

20 Claims, 4 Drawing Sheets though these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

DEVICE FOR RECORDING AND TRANSFERRING A CONTOUR

BACKGROUND OF THE INVENTION

1. Field of the Invention

The invention relates to a device for appliances for ostomy, fistula, wound or drain site treatment.

In connection with surgery for a number of diseases in the gastro-intestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Wafers of appliances for ostomy, fistula, wound or drain site treatment are manufactured in a variety of different standard shapes, sizes and configurations to meet the many different needs of the users. Although these standard products meet the needs of the average user, they do not ideally meet the needs of any particular individual. In most cases, the user must adapt the product prior to use to suit his or her anatomy or lifestyle. Typical modifications, which can be performed include cutting of the aperture in the wafer for receiving the wound or opening in tissue the wafer. Where the aperture for a stoma may be substantially the same for the same patient and thus a number of wafers may be provided with an aperture custom made for this particular patent, a wound or fistulae may change contours and size over time and thus a new customized aperture has to be made for each appliance.

2. Description of the Related Art

Methods for recording the size and shape of wounds are well known:

In EP patent application No. EP 730 845 is disclosed a device for measuring wound surface. The device is in the form of a transparent sheet being folded to provide two superimposed sheets. A perforated line may separate the sheets from each other's. The double layer is placed over the wound; the contours of the wound are marked with a marking device on the top layer. Then the second layer, facing the wound and being smeared by wound exudates, are removed by tearing along the perforated line. The sheet with the markings is saved in the patients file.

U.S. Pat. No. 5,265,605 discloses a wound assessment tool in the form of a first transparent sheet, adhered to a second transparent sheet. The combined sheets are placed over the wound, the contours of the wound are marked up on the upper sheet, and then the lower sheet is removed and discarded, and the upper sheet, with the drawing of the wound, is saved for the record in the patients file.

EP patent application No. EP 640 332 discloses a wound dressing in a package, wherein the package may be used as a wound assessment tool. One side of the package serves as a protection layer against exudates from the wound while the other layer is for recording the size of the wound. The protection layer is discarded after use and the record layer is saved for the file.

None of the above-mentioned references provides a method for transferring the image of the wound to an appliance, on the contrary, if they were used for this purpose a mirror image would occur on the appliance, which would be unusable for this purpose.

Methods for preparing customized apertures in ostomy appliances are also known. In EP Patent No. 1 124 516 is disclosed a method for making a customized ostomy appliance comprising the steps of: measuring the outer contour of the stoma of the patient, recording the information relating to the measurements and transforming the recorded information into electronic form, and utilizing the information for printing a cutting guide pattern on a material for adhering to the adhesive wafer of the appliance. The method is only applicable when a large number of identical apertures are desired.

Thus there is still a need for a device for recording and transferring an image of a wound or opening in tissue to an appliance for ostomy, fistula, wound or drain site treatment.

SUMMARY OF THE INVENTION

It is an object of the present invention to be able to trace the contours of a wound or opening and transfer the tracing in an easy and accurate manner to an appliance.

It is further an object of the present invention to provide a method for tracing and transferring an image of a wound or opening.

It is still further an object of the present invention to provide an appliance with a customized aperture for receiving a wound or opening.

BRIEF DESCRIPTION OF THE DRAWINGS

The invention is disclosed more in detail with reference to the drawings in which.

DETAILED DESCRIPTION OF THE PRESENT INVENTION

Figure 1:
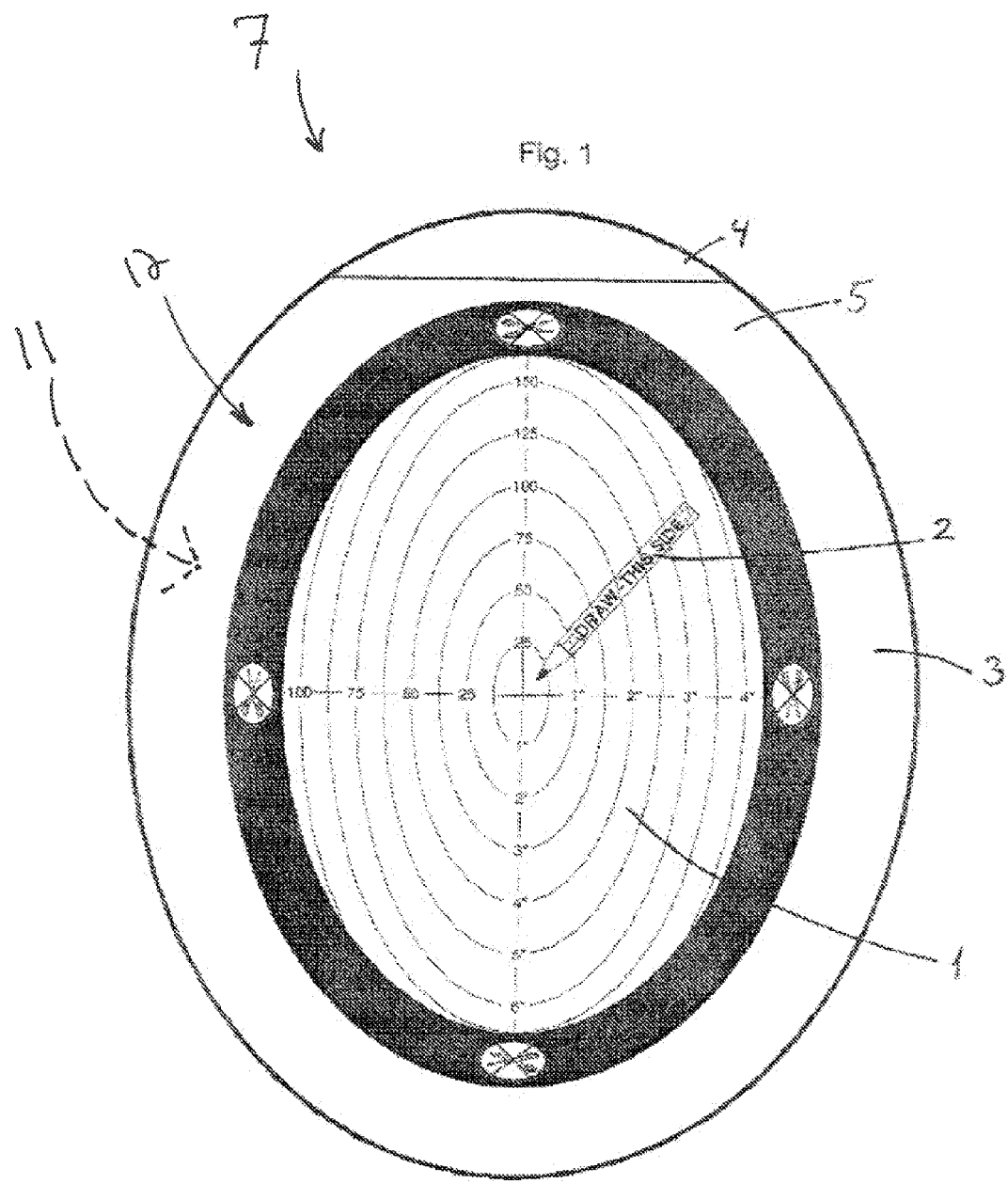
FIG. 1 shows a preferred embodiment of the invention seen from the non-skin facing side.

The invention relates to a device for recording the contours of a wound or opening in tissue of a human being comprising a transparent polymer sheet having a first and a second surface, wherein the first surface faces the wound or opening and the second surface comprises a central portion and an edge portion wherein the edge portion is provided with an adhesive layer.

By suitable for drawing is meant a surface to which it is possible to draw with e.g. a speed marker, pencil, ball-pen or other drawing tools. Some surfaces, e.g. coatings such as Teflon may repel any kind of drawing tools, the ink will glance off, and such surface would be unsuitable for drawing.

Devices for recording size and shapes of wounds or openings in tissue often suffer from the drawback that the size is recorded by placing a transparent sheet over the wound or opening, tracing the outline of the wound or opening and then mounting the sheet on the skin-facing surface of an adhesive wafer of a collection bag. However, in doing so, the transferred image will be mirrored on the wafer. Working with ostomy openings this may be a minor problem as these may be substantially round or symmetric, but in the handling of wounds or fistulae, the contours may be quite asymmetric and irregular, thus a mirror image may not fit at all.

A way of avoiding this mirror image is to trace the contours of the wound onto a transparent sheet, cutting the sheet along the contours, reversing the sheet and use it as a template for drawing the mirror-image on the wafer and then cutting the wafer. However, this method may be laborious and inaccurate.

A record of the contours of a wound or opening may be transferred to the non-skin-facing surface of the wafer, thus the mirror problem is avoided. However, this surface of the wafer is usually occupied by coupling means and/or collection bags and is thus highly unsuitable for this use.

In the treatment of wounds or fistulae, it is important the wafer of the appliance is fitting precisely around the wound or opening. If the aperture is too large, the effluent from the wound or opening may soak the surrounding healthy skin, thus giving rise to maceration of the skin, furthermore while washing/cleaning of the wound the washing fluids may also damage the skin. So, a snug fit around the wound or opening is crucial.

By using the device of the present invention it has surprisingly been shown that an accurate record of the wound or opening may be obtained and transferred to the adhesive wafer of appliance.

The present invention improves the precision of transferring the contours of a wound from a patient to a product as the recorded contours may be used directly for cutting without being redrawn.

Furthermore, the invention simplifies the work, makes it easier for the user to transfer the contours of a wound or opening from a patient to an appliance.

The present invention makes it unnecessary to apply a label or a print onto the backing of an application, as all the necessary inscriptions can be applied to the application by attaching the device of the invention to the application.

The second surface, facing away from the wound is adapted to be marked upon, by tracing the outline of the wound or opening. For tracing a marking pen or other suitable device may be used. Preferably the central portion is non-adherent.

In order to avoid wrong use of the sheet, the wound facing surface may be provided with properties, e.g. in the form of a coating which renders it difficult or impossible to mark upon. Such coating may be in the form of a silicone, Teflon or the like. Or the sheet may be in the form of a laminate where the material of the second surface has inherent properties for repelling ink or the like. The user will note that the making pen is not able to draw on the coated surface when it is used in the wrong position, and thus the user may turn it upside down into correct position and continue tracing.

The adhesive layer may be in the form of a pattern of adhesive and non-adhesive areas or it may be in the form of a homogenous coating. As the function of the adhesive is to hold the sheet fixed to the adhesive wafer during cutting or transfer of the contours, the amount and distribution of the adhesive is not restricted to any particular form as long as the function of fixating the sheet to the wafer is present. The adhesive layer may e.g. be in the form of separate or connected dots or lines of adhesive. The skin-facing surface of the adhesive wafer may typically be provided with a protective release liner, such as a siliconised paper to be removed before application to the body part. The device of the invention may be attached to this release liner before cutting.

After cutting, the release liner on the adhesive wafer may then be removed together with the device of the invention and saved as documentation of the patients wound condition historically.

The adhesive may in one embodiment of the invention be in the form of a low tack adhesive, i.e. a "post-it" adhesive which may be attached and detached several times. This opens for the possibility of repositioning the sheet for correction, and after cutting to remove the sheet from the wafer and store it in the patients record. The storage of the record may also be achieved by removing the release liner of the wafer, carrying the sheet and store this laminate in the file.

It is preferred that the sheet, especially the central portion, is having indicia thereon which allows a user to determine the contours of a wound. The indicia may be in the form of a grid or a bulls-eye or other kind of suitable markings, helping the user to correct positioning of the sheet and accurate tracing of contours of the wound or opening.

The sheet may be prepared from any suitable transparent material. In order to see the contours of the wound through the material, it has to be provided with a certain transparency or translucency. The hereby used "transparent" is to be interpreted as translucent enough to render the contours of the wound or opening traceable looking through the sheet. Thus a slightly opaque material may also be used. A certain flexibility of the sheet may also be desired as the sheet may be applied to curved body parts such as abdomen, sacrum, arms or legs. The sheet may preferably be prepared from a transparent polymer being selected from the group consisting of polypropylene, polyurethane, polyethylene, polyvinylchloride, polyester, polystyrene and acetate.

The adhesive layer of the second surface may be protected by at least one release liner. The release liner may cover the adhesive layer but not the central portion of the sheet, as this would inhibit the marking process. In a preferred embodiment of the invention the device comprises at least two release liners, a first liner exposing a small area of the adhesive layer when removed, and a second liner covering a the residual surface of the adhesive layer. The first liner may be removed first and the sheet is positioned at the adhesive wafer. When correct positioning is achieved, the adhesive maintains the position and then the second liner is removed and the device is adhered to the wafer.

Thus, a first release liner may be present for exposing only a small area of the adhesive layer. This is done to make it easier for the user to achieve correct position of the device onto the wafer.

In one embodiment of the invention the entire second surface of the present invention is provided with an adhesive coating, but the central portion is further provided with a non-adhesive, transparent layer, suitable for drawing. The non-adhesive transparent layer may cover the entire adhesive surface of the second layer, but the central portion and the edge portion of this non-adhesive transparent layer may be parted, e.g. by kiss-cutting a line separating the two portions. The non-adhesive transparent layer part covering the edge portion may thus serve as protective release liner for the adhesive, while the center portion of said layer may be used for drawing. This embodiment of the invention facilitates easy production of the device.

The first surface is provided with a transparent protection layer. The protection layer serves to protect the sheet from getting smudgy by the exudates from the wound or opening, and is used during marking up the wound or opening and then removed and discarded before applying the device to the wafer. The protective layer may be in the form of a separate layer or it may be attached to the sheet. Attachment may be in the form of adhesive or welding along the edge portion or a continuation of the sheet being folded and preferably provided with a tear line for separation the two layers. In one embodiment of the invention the protective layer is adhered without application of adhesive but utilizing inherent adhesive properties of the material, e.g. like cling-film. The protective layer may be substantially the same size as the device of the invention or it may be larger.

The invention further relates to a method for recording the contours of a wound or opening in the tissue of a human being comprising the steps of:
a) covering the wound or opening with a transparent polymer sheet having a first and a second surface, wherein the first surface faces the wound or opening and the second surface comprises a central portion and an edge portion wherein the edge portion is provided with an adhesive layer,
b) tracing the contours of the wound or opening on the central portion of the second surface of the sheet,
c) removing the sheet from the wound or opening,
d) attaching the adhesive layer of the second surface of the sheet to the skin-facing surface of an adhesive wafer of an appliance for ostomy, fistula, wound or drain site treatment,
e) cutting an aperture in the adhesive wafer for receiving the wound or opening.

When the wafer has been cut the polymer sheet of the invention may be removed from the wafer and saved for the patients file. In one embodiment of the invention the sheet is removed together with the release liner of the adhesive wafer.

Preferably, a transparent protection layer is placed between the wound and the transparent sheet in order to avoid smudging of the sheet. The protection layer may be a part of the device of the invention or it may be a separate layer.

The invention further relates to a kit comprising an appliance for ostomy, fistulae, wound or drain site treatment and a transparent polymer sheet having a first and a second surface, wherein the first surface faces the wound or opening and the second surface comprises a central portion and an edge portion wherein the edge portion is provided with an adhesive layer.

The central portion is preferably non-adherent in order to facilitate marking of the wound or opening.

The adhesive layer may be in the form of a pattern of adhesive and non-adhesive areas.

The central portion has preferably indicia thereon which allows a user to determine the contours of a wound. The indicia may be in the form of a printed pattern such as a grid or bull-eye.

The transparent polymer may preferably be selected from the group consisting of polypropylene, polyurethane, polyethylene, polyvinylchloride, polyester, polystyrene and acetate.

The adhesive layer may be protected by at least one release liner.

The kit may further enclose a transparent protection layer for placing between the first surface of the sheet and the wound or opening. The protection layer may be in the form of a transparent cover or film, which is placed over the patient in order to prevent any exudates from the wound or opening from getting in contact with the polymer sheet. Hereby the hygienically status of the product is preserved.

By using the kit of the present invention for tracing the size of a wound or opening, the work will be eased for the user and the accuracy of the transfer of the markings will be improved.

When the contours of the wound or opening have been marked up on the transparent polymer sheet, the sheet constitutes a piece of documentation showing cut-zone information and size of wound.

In order to prevent the user in turning the device upside down when tracing the contours of the wound, the first surface of the sheet may be provided with a description or an illustration, illustrating the user which side to orientate upwards before drawing onto it. Furthermore, the first surface of the sheet may be siliconised or treated in other way in order to make the surface repel the marking tool. The same material characteristic may be obtained by using a laminate material having different properties for each surface. Thus, it may be prevented that the user traces the contours of the wound or opening to the wrong side of the sheet.

The device of the present invention may further more be provided with a description or illustration that informs the user about the boundaries for where to cut or not to cut, grid for measuring the width and the length of a wound, marked space for writing initials of patient, date of treatment etc.

The central portion of the second surface of the device of the present invention is prepared from a transparent or translucent film material that can be drawn on with a permanent pen, Indian ink or other form of marking pens without being able to smear off easily.

This second surface of the flexible transparent sheet is preferably provided with a central non-adhesive portion and a peripheral adhesive portion.

The central, non-adhesive portion is preferably not covered by a release liner. The adhesive portion is preferably covered by at least one release liner that does not cover the portion of the surface that the user may provide with markings.

After having attached the transparent polymer sheet onto the skin-facing surface of the wafer, the user then may cut the laterally reversed markings with e.g. a pair of scissors or a knife directly through the sheet.

The use of these means will ease the work and improve accuracy in transferring a drawing of a wound or opening onto a wafer for ostomy, fistula, wound or drain site treatment.

The use of these means will make it unnecessary to apply any label or print onto the application, where the necessary inscriptions can be applied onto the application secondary. The aperture is cut directly from the recorded contour, the contours have not been redrawn or transferred to a label and thus the risk of inaccuracies is decreased. Of course it would be possible to record the contours on the device of the invention, cut the aperture in the sheet, place it in correct orientation on the wafer, use the cut-out as a template for redrawing the contours on the wafer, remove the device and cut the wafer after the redrawn contours. However, the method is unnecessarily laborious and the accuracy of the drawing may be decreased.

The adhesive wafer of an appliance for ostomy, fistula, wound or drain site treatment may be made from any appropriate skin friendly material known per se for the purpose and may also comprise a top film known per se. The skin-friendly adhesive may be any skin-friendly adhesive known per se, e.g. an adhesive comprising hydrocolloids or other moisture absorbing constituents for prolonging the time of use. The appliance may be provided with attachment means for attaching for example an collection bag or a lid and may be a system known per se comprising matching coupling rings or matching flanges and adhesive surfaces.

The appliance may comprise any suitable conventional collection bag known per se.

The also relates to the use of a device according to claim 1 for tracing the contours of a fistulae or wound. Furthermore the invention relates to the use of a device according to claim 1 for tracing the contours of an ostomy.

DESCRIPTION OF THE PREFERRED EMBODIMENTS

The invention is now explained more in detail with reference to the drawings showing preferred embodiments of the invention. However, it should be understood that the detailed description and specific examples, while indicating at least one preferred embodiment of the invention, are given by way of illustration only, since various changes and modifications within the spirit and scope of the invention will become apparent to those skilled in the art from this detailed description.

In FIG. 1 is shown a preferred embodiment of the invention. The device 7 comprises a polymer sheet having a first surface 11 provided for facing the wound and a second surface 12. The second surface 12 is provided with a central, transparent portion (1) with marking for aiding the registration of the wound or opening, in the form of a bulls-eye grid, and indications (2) for ensuring that the orientation of the device is proper. Furthermore, the second surface 12 is provided with an adhesive border (3) or layer (3) for securing the device to an appliance. The border (3) is not necessarily transparent, it is not of importance whether this portion is transparent or not. The adhesive layer (3) is protected by a large release liner (4) and a small release liner (5). When the small release liner (5) is removed, the exposed adhesive is used for positioning the sheet correctly. When position is proper, the large release liner (4) is removed and the rest of the adhesive layer of the device is adhered to the application.

Figure 2:
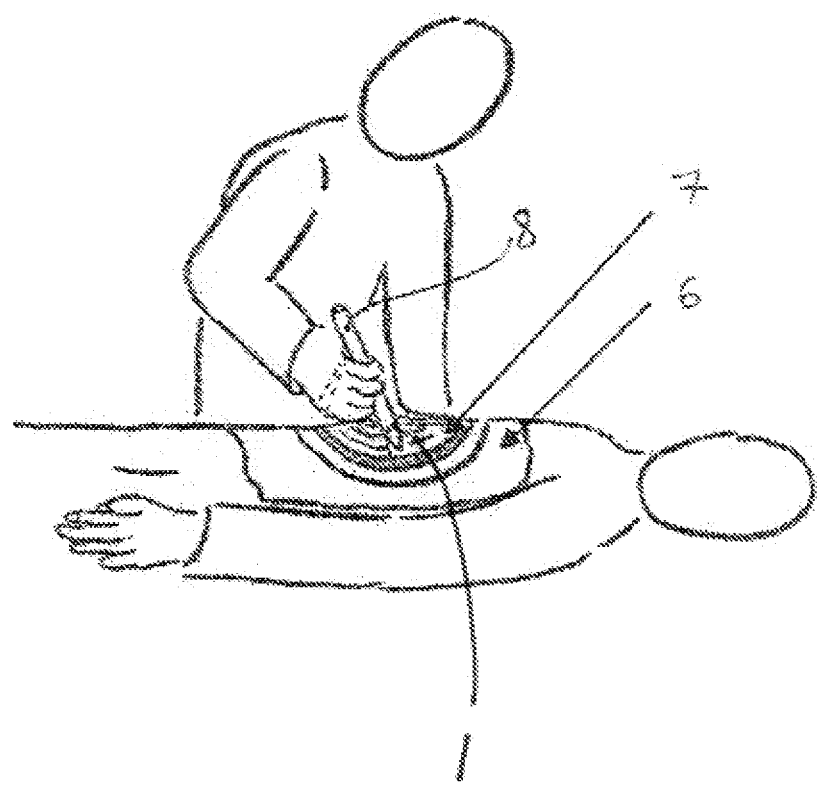
FIG. 2 shows tracing of a wound or opening on the device of the invention.

In FIG. 2 is shown tracing of the contours of a wound. The wound is covered with a transparent protection layer (6) for sanitary precautions and for avoiding exudates on the device 7 of the invention. The device 7 of the invention is placed over the wound or opening with the surface comprising the adhesive border (3) facing away from the wound. The contours are traced with a marking pen (8) on the central portion (1) (See FIG. 1) of the device (7).

Figure 3:
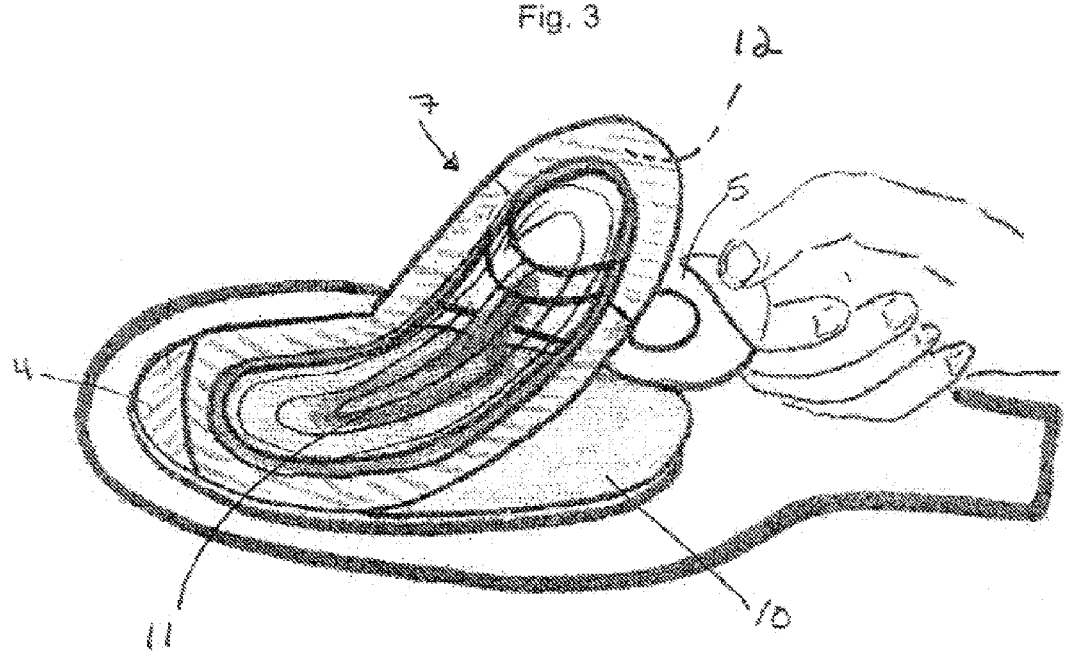
FIG. 3 shows the application of the device of the invention to an appliance and FIG. 4 shows cutting the combined appliance and device.
Figure 4:
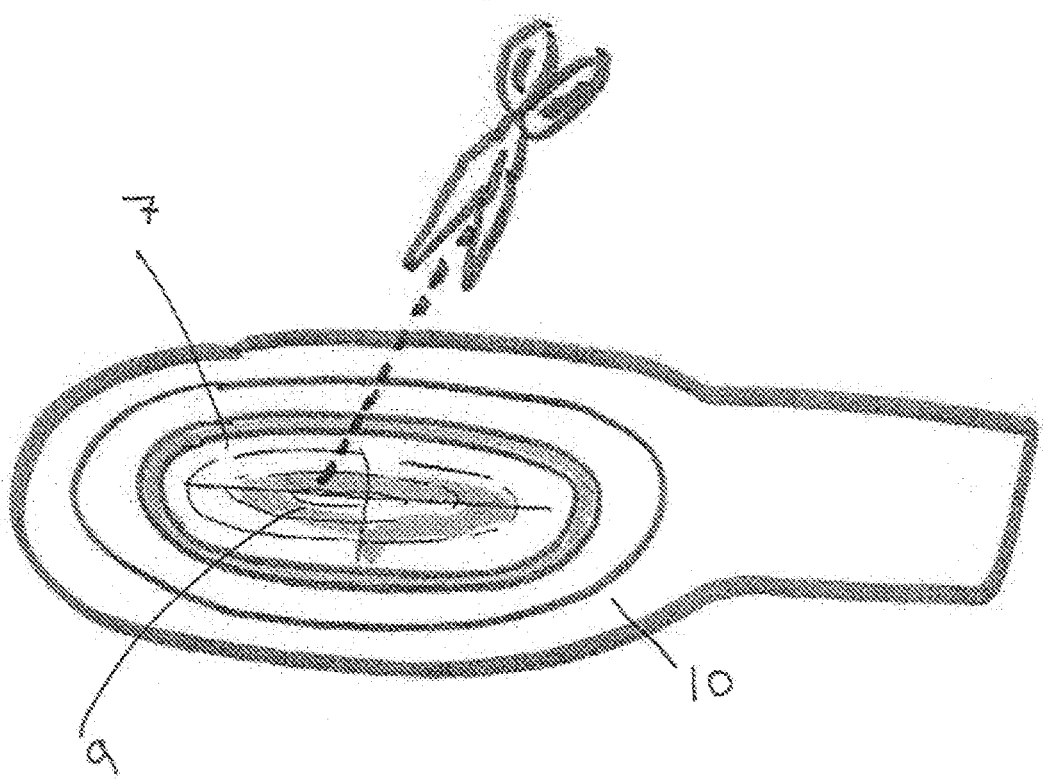

Then the device 7 is removed from the patient and the protection layer (6) is discarded. The device 7 is reversed, the first release liner (4) is removed, and the device 7 is positioned on the skin-facing surface of an appliance 10 (FIG. 3). The exposed adhesive (3) area fixes the device 7 to the appliance 10. Then the second release liner (5) is removed and the device 7 is adhered to the appliance 10, showing a mirror image of the wound or opening. Finally, the combined appliance 10 and device 7 are cut (FIG. 4) along the traced contours in order to provide an aperture in the adhesive wafer of the appliance for obtaining the wound or opening. Thus the cutting is on the line drawn directly from the wound or opening and the drawing need not be transferred and redrawn. In this manner the accuracy of the cutting is improved and a snug fit to the wound or opening is achieved.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A device for transferring tissue contours of a wound or opening onto an adhesive wafer of a wound appliance, the device comprising:
   a transparent polymer sheet having a first non-adhesive surface and a second surface opposite the non-adhesive surface;
   said second surface opposite the first non-adhesive surface including a central portion and an edge portion surrounding the central portion, the edge portion including an adhesive, said central portion being configured to receive a drawn image of a tissue contour;
   said first non-adhesive surface of the transparent polymer sheet being adapted to non-adhesively contact tissue of the patient when the device is in use and the image is being drawn on the central portion, said second surface with said adhesive on the edge portion facing away from the patient when the image is drawn;
   said adhesive of the second surface being attachable to an adhesive wafer of the wound appliance to directly impart the drawn image thereto while said second surface adhesive does not contact the patient; and
   the adhesive having a first part that is covered by a first removable release liner and a second part that is covered by a second removable release liner, the second release liner being larger than the first release liner, the first release liner being removed first to enable the first part of the adhesive to be secured to a wafer when the device is properly aligned, the second release liner being removed thereafter to enable the second part of the adhesive to be secured to the wafer.

2. The device according to claim 1, wherein the central portion is non-adherent.

3. The device according to claim 1, wherein the central portion is receptive to receiving ink drawings.

4. The device according to claim 1, wherein the adhesive on the edge portion is in the form of a pattern of adhesive and non-adhesive areas.

5. The device according to claim 1, wherein the central portion includes indicia provided to allow a user to determine the contour of the wound.

6. The device according to claim 1, wherein the transparent polymer sheet is fabricated from a polymer selected from the group consisting of polypropylene, polyurethane, polyethylene, polyvinylchloride, polyester, polystyrene and acetate.

7. The device according to claim 1, wherein the transparent polymer sheet is one of a translucent polymer sheet and an opaque polymer sheet.

8. The device according to claim 1, further comprising:
   a transparent protection layer that is attachable to the non-adhesive surface of the transparent polymer sheet without using an adhesive, the transparent protection layer provided to be placed between the tissue of a patient and the non-adhesive surface of the transparent polymer sheet.

9. The device according to claim 1, wherein the non-adhesive surface includes a coating that repels ink.

10. The device according to claim 1, wherein said second surface is covered in its entirety with an adhesive coating, and said adhesive coating is covered in its entirety by a non-adhesive transparent layer having a first portion and a second portion separable from one another along a line, said edge portion being covered by said first portion and said central portion being covered by said second portion, said first portion being removed prior to attaching the adhesive edge portion to the adhesive wafer while said second portion remains on said central portion and is configured to receive the drawn image.

11. A device for transferring tissue contours onto an adhesive wafer of a wound appliance, the device comprising:
    a transparent polymer sheet having a first non-adhesive surface and a second surface opposite the non-adhesive surface;
    said second surface opposite the non-adhesive surface including a central portion and an edge portion surrounding the central portion, the central portion being without adhesive and the edge portion including an adhesive;
    a transparent protection layer that is attachable to the non-adhesive surface of the transparent polymer sheet without using an adhesive, the transparent protection layer provided to be placed between the tissue of a patient and the non-adhesive surface of the transparent polymer sheet when drawing an image of a tissue contour onto the central portion of the second surface; and said adhesive of the second surface being attached to the wound appliance so that the central portion of the second surface with the drawn image of the tissue contour contacts the adhesive wafer of the wound appliance and is directly imparted to the adhesive wafer.

12. The device according to claim 11, wherein the central portion is non-adherent and is receptive to receiving ink drawings.

13. The device according to claim 11, wherein the adhesive on the edge portion is in the form of a pattern of adhesive and non-adhesive areas.

14. The device according to claim 11, wherein the central portion includes indicia provided to allow a user to determine the tissue contour.

15. A method for transferring tissue contours of a wound or opening of a patient onto an adhesive wafer of a wound appliance, the method comprising:

providing a device including a transparent polymer sheet having a first non-adhesive, skin-contacting surface and a second adhesive surface opposite the non-adhesive surface, said second adhesive surface including a central portion and an edge portion surrounding the central portion, said second adhesive surface being covered by a non-adhesive transparent layer having a first portion and a second portion separable from one another, the first portion covering the edge portion and the second portion covering the central portion;

placing the device over the wound or opening with the first non-adhesive side facing the patient and drawing an image of a tissue contour onto the central portion of the second surface;

removing the first portion of the non-adhesive transparent layer to expose the adhesive edge portion;

attaching the adhesive edge portion of the second surface to the adhesive wafer of the wound appliance so that the central portion of the second surface with the drawn image of the tissue contour contacts the adhesive wafer of the wound appliance and the drawn image is directly imparted to the adhesive wafer, said adhesive layer not coming into contact with patient tissue; and cutting an opening in the wafer and device that follows the drawn image.

16. The method as set forth in claim 15, further comprising, before the step of drawing, the step of:

placing a transparent protection layer between the wound or opening in the tissue of a patient and the non-adhesive surface of the transparent polymer sheet.

17. The method as set forth in claim 15, wherein the device further comprises the adhesive layer having a first part that is covered by a first removable release liner and a second part that is covered by a second removable release liner, the second release liner being larger than the first release liner, the step of attaching the adhesive layer including the steps of:

removing the first release liner and securing the first part of the adhesive layer to the wafer when the device is properly aligned; and removing the second release liner thereafter to enable the second part of the adhesive layer to be secured to the wafer.

18. The method as set forth in claim 15, further comprising the step of separating the adhesive layer of the second surface from the wafer to remove the device from the wafer after the opening is cut out.

19. A device for transferring tissue contours of a wound or opening onto an adhesive wafer of a wound appliance, the device comprising:

a transparent polymer sheet having a first non-adhesive surface and a second surface opposite the non-adhesive surface, the first non-adhesive surface including a coating that repels ink;

said second surface opposite the first non-adhesive surface including a central portion and an edge portion surrounding the central portion, the edge portion including an adhesive, said central portion being configured to receive a drawn image of a tissue contour;

said first non-adhesive surface of the transparent polymer sheet being adapted to non-adhesively contact tissue of the patient when the device is in use and the image is being drawn on the central portion, said second surface with said adhesive on the edge portion facing away from the patient when the image is drawn;

said adhesive of the second surface being attachable to an adhesive wafer of a wound appliance to directly impart the drawn image thereto while said second surface adhesive does not contact the patient.

20. A device for transferring tissue contours of a wound or opening onto an adhesive wafer of a wound appliance, the device comprising:

a transparent polymer sheet having a first non-adhesive surface and a second surface opposite the non-adhesive surface;

said second surface opposite the first non-adhesive surface including a central portion and an edge portion surrounding the central portion, the edge portion including an adhesive, said central portion being configured to receive a drawn image of a tissue contour;

said first non-adhesive surface of the transparent polymer sheet being adapted to non-adhesively contact tissue of the patient when the device is in use and the image is being drawn on the central portion, said second surface with said adhesive on the edge portion facing away from the patient when the image is drawn;

said adhesive of the second surface being attachable to an adhesive wafer of a wound appliance to directly impart the drawn image thereto while said second surface adhesive does not contact the patient; and said second surface being covered in its entirety with an adhesive coating, said adhesive coating being covered in its entirety by a non-adhesive transparent layer having a first portion and a second portion separable from one another along a line, said edge portion being covered by said first portion and said central portion being covered by said second portion, said first portion being removed prior to attaching the adhesive edge portion to the adhesive wafer while said second portion remains on said central portion and is configured to receive the drawn image.

* * * * *